United States Patent [19]

Barberet et al.

[11] Patent Number: Plant 7,178

[45] Date of Patent: Mar. 6, 1990

[54] CARNATION NAMED LONSIMLIZ

[75] Inventors: Nicole Barberet; Henri Blanc, both of Antibes, France; Antonio Di Giorgio; Renato Di Giorgio, both of San Remo, Italy

[73] Assignee: Etablissements Barberet et Blanc, La Londe-Les-Maures, France

[21] Appl. No.: 315,023

[22] Filed: Feb. 24, 1989

[51] Int. Cl.[4] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new and distinct standard carnation cultivar particularly distinguished by its profuse production of medium sized blooms having a light yellow coloration, with petals having margins of dark violet coloration, said dark violet coloration is also present in short marks extending inwardly into the petals from the margins. The blooms are borne singly on long, strong, upright stems, the plant reaching a height of about 140 cm at eight months of growth, and having a recurrent blooming habit with moderately abundant foliage.

1 Drawing Sheet

BACKGROUND OF THE NEW PLANT

This new carnation plant originated at San Remo, Italy, in 1985, as a seedling derived from our crossing plants selected from breeding stock maintained in our greenhouse at San Remo, Italy. The object of this crossing being the production of an improved carnation suitable for cut flowers. It was discovered that the plant possessed the precocity and color contrast that we were seeking as well as a profuse production of medium sized flowers borne on the strong, upright stems of a tall plant having a height of about 140 cm at eight months growth. Asexual propagation of this new plant, by means of cutting has been carried out under our direction at San Remo through successive generations, and the distinctive characteristics of this plant have been found to hold true from generation to generation and appear to be firmly fixed.

Accordingly, our new carnation variety is now being propagated for commercial purposes by means of cuttings, as well as by in vitro propagation procedures, at Establissements Barberet et Blanc, Laboratoire de Physiologie Vegetale, 83250 La Londe-Les Maures, France.

DESCRIPTION OF THE DRAWING

Our new carnation variety is illustrated by the accompanying photographic drawing, which shows several blooming stems with flowers and buds in several stages of development, the color rendition being as nearly true to that herein specified as as reasonably possible to obtain by professional photographic procedures.

DESCRIPTION OF THE NEW PLANT

The following is a detailed description of our new carnation variety based upon observations made in the Spring of 1988 of plants grown in greenhouse, as well as outside, at San Remo, Italy, the color designations stated herein being according to The R.H.S. Colour Chart published by The Royal Horticultural Society of London, England.

THE PLANT

Origin: Seedling.

Parentage:

*Seed parent.*—Variety No. 490.

*Pollen parent.*—Variety No. 647.

Both parents are unpatented and unnamed and are identified in the breeding records maintained in the Di Giorgio nursery office at Via Villetta 41, 18038 San Remo, Italy.

Classification:

*Botanic.*—*Dianthus caryophyllus.*

*Commercial.*—Standard Carnation.

Form: A tall, erect bush having at least four stems emitted near the ground.

Height: Averages about 140 cm at eight months of growth.

Main stem length: Less than 15 cm due to pinching to foster branching.

Branching: This plant is well branched.

Growth: Vigorous and upright.

Foliage:

*Quantity.*—Moderately abundant.

*Number of leaves.*—More than 120.

*Leaf size.*—(At the seventh node) About 10 cm long and about 0.98 cm wide.

*Leaf shape.*—Oblong — with rolled up margins.

*Texture.*—Leathery.

*Color.*—Both upper and under sides, 189-A/B.

THE BUD

Size: Large.

*Diameter.*—Averages about 2.2 cm.

*Length.*—Averages about 3.5 cm.

Shape: Ovoid.

Rate of opening: Normal.

Color of petals: When sepals first divide and petals begin to unfurl: the same as at full bloom.

Sepals:

*Number.*—Seven.

*Shape.*—Generally ovoid, with acuminate tip and joined together at the lower parts.

*Character.*—The sepals are hooded over the bud before they divide and stand up when the flower opens. They are not branched.

*Color.*—Inside, 145-B and 185-C; outside, 137-C and 144-C.
*Striae.*—Longitudinal.

Calyx:
*Shape.*—Funnel-shaped.
*Size.*—Large.
*Aspect.*—Smooth.
*Splitting.*—Sometimes a little splitting occurs.

Flower stem:
*Length.*—About 73.6 cm, average, when cut at the tenth node.
*Character.*—Rigid and erect.
*Color.*—189-A/B.

THE FLOWER

Blooming habit: Recurrent, blooming profusely in the Spring, Midseason and Fall blooming periods with a tendency to give few blooms in the Fall.

Size of flower: Large.
*Diameter.*—Averages about 10 cm.
*Depth.*—Averages about 4.5 cm.

Borne: Singly, on a long, strong, upright stem.

Shape: When bloom first opens, high-centered. When bloom matures, ball-shaped.

Petalage:
*Number of petals.*—Averages about 116.
*Arrangement.*—Imbricated.
*Form.*—Fan-shaped with serrated outer end margins. The outer petal is large.
*Texture.*—Leathery.
*Aspect.*—Santiny.
*Color.*—Both inner and outer petals — Body: Bright yellow, 2C. Margin and marks; Dark violet, 71B. Base: Yellowish white. Reverse side: 1D and 71B.

Petaloids:
*Number.*—Less than six.
*Size.*—Smaller than the petals.
*Color.*—The same as the petals.

Flower stem:
*Character.*—Upright with good strength.
*Length.*—Averages about 73.6 cm when cut at the tenth node.
*Color.*—Green, R.H.S. 189 A/B.

Discoloration after full bloom: Very little.

Persistence: The flower petals hang on and dry.

Fragrance: Perceptible.

Lasting quality: As a cut flower, at least ten days in vase keeping.

REPRODUCTIVE ORGANS

Stamens:
*Number.*—About 16.
*Arrangement.*—Encircling the ovary.
*Anthers.*—Size: Less than 4 mm. Color: Yellowish.
*Filaments.*—Length: Average about 3.2 cm. Color: Yellowish.

Pistils:
*Number.*—Four.
*Styles.*—Length: About 3 cm. Color: Slightly pink.
*Stigma.*—Color: Slightly pink.

Character of ovaries: Ribbed.

This carnation variety most nearly resembles the variety Original (unpatented).

We claim:

1. A new and distinct standard variety of carnation plant substantially as herein shown and described, particularly distinguished by its profuse production of medium sized light yellow blooms with petals having margins of dark violet and short dark violet marks extending inwardly into large sized petals, borne singly on long, strong, upright stems of a vigorous, tall plant having moderately abundant foliage.

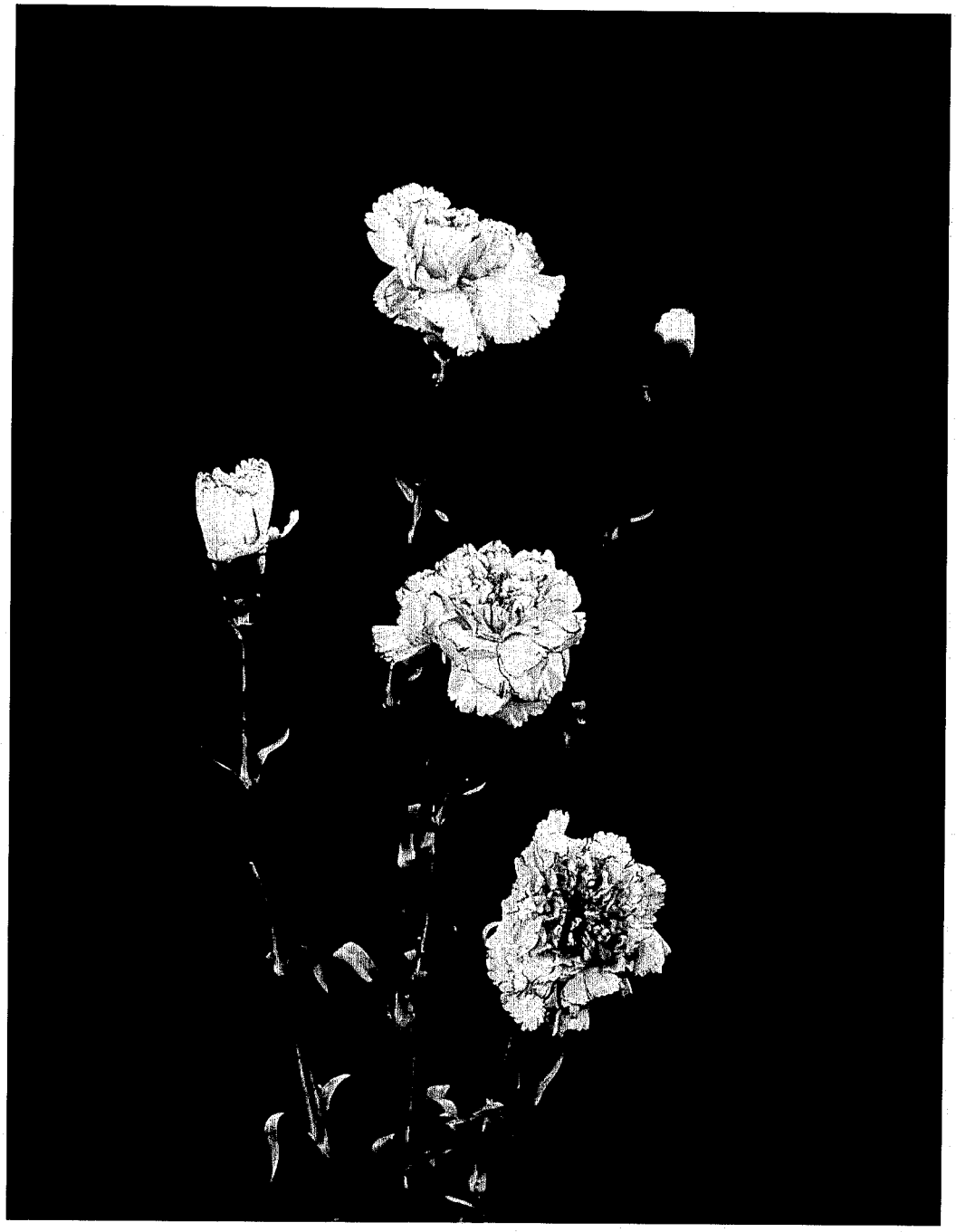

* * * * *